United States Patent [19]

Butler

[11] 4,006,059

[45] Feb. 1, 1977

[54] HYDROPHOBIC NONCOVALENT BINDING OF PROTEINS TO SUPPORT MATERIALS

[75] Inventor: Larry G. Butler, West Lafayette, Ind.

[73] Assignee: Purdue Research Foundation, West Lafayette, Ind.

[22] Filed: July 29, 1974

[21] Appl. No.: 492,508

[52] U.S. Cl. .................................. 195/68; 195/63; 195/DIG. 11; 260/112 R
[51] Int. Cl.² ......................................... C07G 7/02
[58] Field of Search .............. 195/63, 68, DIG. 11; 260/112 R; 424/94

[56] References Cited

UNITED STATES PATENTS 3,909,360   9/1975   Horiuchi et al. ................. 195/63 X

OTHER PUBLICATIONS

Er-el, et al., Hydrocarbon-coated Sepharoses, Bichem. and Biophys. Res. Comm., vol. 49 No. 2, 1972, (pp. 383-390).

Yon; R. J. Enzyme Purification by Hydrophobic Chromatography, Biochem. J. vol. 137, Jan. 1974. (pp. 127-130).

Zaborsky; O., Immobilized Enzymes, CRC Press. Cleveland, Ohio, 1973 (pp. 79-82).

Hofstee; B. H. J., Protein Bonding by Agarose Carrying Hydrophobic Groups in Conjunction with Charges, Biochem. and Biophys. Res. Comm. vol. 50, No. 3, 1973 (pp. 751-757).

Hofstee; B. H. J., Hydrophobic Affinity Chromatography of Proteins. Analytical Biochemistry, vol. 52, 1973 (pp. 430-433 and 444-448).

*Primary Examiner*—David M. Naff
*Attorney, Agent, or Firm*—John R. Nesbitt

[57] ABSTRACT

Proteins such as enzymes are noncovalently immobilized by treating a hydrophilic support material having hydroxyl or amino groups with an acid chloride of a hydrophobic acid such as phenoxyacetyl choride and to the resultant hydrophobic support material adsorbing a protein.

5 Claims, No Drawings

HYDROPHOBIC NONCOVALENT BINDING OF PROTEINS TO SUPPORT MATERIALS

This invention described herein was made in the course of, or under, a grant from the National Institutes of Health, Department of Health, Education and Welfare.

FIELD OF THE INVENTION

This invention relates to binding of proteins to support materials and more particularly relates to strong hydrophobic noncovalent binding of proteins to support materials.

BACKGROUND OF THE INVENTION

In recent years proteins and enzymes have been immobilized on a variety of support materials, and such immobilization has commonly been achieved by covalent attachment, entrapment in hydrophilic gels, or by adsorption. Immobilized enzymes have attracted considerable attention because of their advantages of economy (expensive enzymes can be readily recovered and reused), convenience (immobilized enzymes can be removed readily without contaminating the solution being treated), and stability (most enzymes are more stable when immobilized). The advantages and uses of immobilized enzymes have been summarized in several reviews: Silman and Katchalski, Ann. Rev. Biochem. 35, 873 (1966); Vieth and Venkatasubramanian, Chem. Tech. 677 (1973), 47 (1974); Zaborsky, New Scientist, 719 (1973); Goldstein, Methods Enzymol. XIX, 935 (1970), Mosback, Sci. Amer. 224(3), 26 (1971).

Methods for immobilization of proteins by either covalent attachment or by entrapment in gels usually require somewhat exotic chemistry, and/or expensive and sometimes toxic reagents. Moreover, usually only a small portion of the protein supplied actually becomes immobilized and biologically active. In contrast, immobilization by adsorption is much more convenient and inexpensive because no covalent chemical bond is formed between the protein and the support. However, adsorption is generally not strong enough to completely immobilize the protein; with some supports, for example, subsequent tanning with formaldehyde is necessary to provide sufficient strong binding [Weston and Avrameas, Biochem. Biophys. Res. Commun. 45, 1574 (1974); Olson and Stanley, Agr. Food Chem. 21, 440 (1973)]. Alternatively, stronger adsorption can be sometimes obtained with specific affinity reagents, however, preparation of these supports again involves rather complex chemistry.

Since most proteins are felt to be associated to some degree with hydrophobic membranes in the cell where they naturally function, they might be expected to similarly associate with artificially supplied hydrophobic materials. Indeed, a few recent reports of hydrophobic chromatography have indicated that proteins can associate with such hydrophobic materials [Er-el, Zaidenzaig and Shaltiel, Biochem. Biophys. Res. Comm. 49, 383 (1972); Hofstee, Anal. Biochem. 52, 430 (1973); Shaltiel and Er-el, Proc. Natl. Acad. Sci. U.S. 70, 778 (1973); and Yon, Biochem. J. 137, 127 (1974)].

Heretofore, however, a hydrophobic support has not been prepared and utilized that achieves substantially complete immobilization by adsorption with no covalent chemical bond being formed between the protein and the support.

SUMMARY OF THE INVENTION

This invention provides a method for preparing simple hydrophobic derivatives of a variety of insoluble matrices, both inorganic and organic, as well as the use of such support materials as strong adsorbants of proteins and enzymes. In many cases the adsorption is sufficiently strong so that the proteins are effectively immobilized and can be utilized in many applications for which much less convenient techniques of immobilization are now being used. The method of this invention can also be applied to binding of proteins by small molecules and biological materials, when suitably modified to introduce the proper hydrophobic groups.

It is therefore an object of this invention to provide a method for preparing support materials that are hydrophobic in nature.

It is another object of this invention to provide a method for preparing a hydrophobic support material that can be utilized for strong noncovalent binding of proteins to such support materials.

It is still another object of this invention to provide a method for preparing a hyrophobic support material suitable for substantially completely immobilizing protein by adsorption.

It is another object of this invention to provide a hydrophobic support material that is utilized to bind proteins and enzymes.

It is yet another object of this invention to provide a method for binding protein and enzymes that includes providing a hydrophobic support material and exposing proteins thereto to cause a strong noncovalent binding therebetween.

It is still another object of this invention to provide a method for substantially completely immobilizing proteins by adsorption that is economical and convenient and is stable.

It is yet another object of this invention to provide a stable protein substantially completely immobilized by adsorption on a hydrophobic support material.

With these and other objects in view which shall become apparent to one skilled in the art as the description proceeds, this invention resides in the novel support and method for forming the same, as well as in the method for binding, substantially as hereinafter described, and more particularly defined by the appended claims, it being understood that such changes in the precise embodiments of the herein disclosed invention are meant to be included as come within the scope of the claims.

DESCRIPTION OF THE INVENTION

This invention is based on a property of proteins which as yet has been hardly exploited as a means for binding. Electrostatic binding of proteins, by virtue of their charged groups, to ionic derivatives of cellulose, for instance, has long been important for protein purification by column chromatography. However, proteins are amphipathic (both hydrophilic and hydrophobic) macromolecules, and although the hydrophobic portion of the molecule may be largely buried in the core of the structure, it is recently being recognized that at least some proteins have an hydrophobic area at the surface [Robillard and Wishnia, Biochemistry 11, 3835, 3841 (1972)]. This site would presumably bind to hydrophobic materials supplied in an aqueous environment. It is likely that such hydrophobic areas are the sites of binding of the protein to a membrane under physiological conditions in the cell.

The preparations which have been found to be most useful have all been esters of hydrophobic acids with the corresponding amides apparently not binding proteins as strongly. The esters have all been prepared by reaction of the acid chloride of a suitably hydrophobic acid with a hydroxyl group in the support material.

In essence, strong noncovalent binding of proteins to hydrophobic derivatives is achieved with binding being sufficiently strong that the protein is effectively immobilized, yet the biological function of the protein is fully expressed. The support material is chemically modified so as to be hydrophobic in nature and the protein exposed thereto, preferably in an aqueous environment.

EXAMPLE I

PREPARATION OF PHENOXYACETYL CELLULOSE.

Whatman cellulose (CF11), 30 grams, was suspended in 300 ml of 1:1 pyridine:dimethylformamide. A total of 21 ml of phenoxyacetyl chloride (Eastman) was slowly added with vigorous stirring resulting in the solution warming somewhat. After 1 ½ hours with occasional stirring, the resulting dark yellow suspension was heated to 70° C, then allowed to stand overnight without further stirring. After decanting off as much solvent as possible, 95% ethanol was added and stirred. The product was recovered by filtration on a Buchner funnel and rewashed several times with ethanol. Since it is difficult to remove all of the solvent it was necessary to resuspend the pad of phenoxyacetyl cellulose each time in fresh solvent rather than just washing it on the filter. The first few washes were quite yellow but the final wash was water clear. The pad of phenoxyacetyl cellulose was partially dried on the funnel and completely dried by spreading it out on a sheet of plastic. From the 30 grams of cellulose, 36 grams of phenoxyacetyl cellulose was recovered. No fines were discarded during the preparation and the material seemed to have a good flow rate when packed into a column. The material is stored dry and appears to be quite stable in this form. The phenoxyacetyl cellulose has a maximum of ½ phenoxyacetyl group per glucose residue. It is slowly wet by water, expanding its volume considerably. On long storage in aqueous media it tends to hydrolyze to give phenoxyacetate and thus lose its capacity to bind protein.

EXAMPLE II

COLUMN TESTING OF PHENOXYACETYL CELLULOSE AS AN AGENT FOR PROTEIN IMMOBILIZATION.

The above phenoxyacetyl cellulose was suspended in water and poured into a column 1.6 cm in diameter by 18 cm in height. The column was washed with several hundred ml of 0.05 M Tris, pH 7.4 and then enzyme was applied. The enzyme solution utilized was a preparation partially purified from bovine intestine, considerably enriched in alkaline phosphatase and phosphonate monoesterase activity; 42 ml of the enzyme preparation in the above buffer was applied. The column was then washed with 50 ml portions successively of a large number of solutions which are described below. After each wash the eluate was tested for the presence of alkaline phosphatase activity and phosphonate monoesterase activity; in no case was any activity found. The following solutions were utilized for washing the column in the order given (all were dissolved in the 0.05 M Tris, pH 7.4): no addition to buffer, then 1.2, 5, and 12 mM pyridine, 5, 10, 25, 50, 100, 200, and 500 mM sodium benzoate, buffer alone again, 3,6, 7.2, 18, 36, 72, and 180 mM phenyl-1,2-ethanediol, 10% ethanol, and 20% ethanol. No enzymatic activity was eluted by any of these solvents. Passage of an assay mix over the column indicated considerable activity of both alkaline phosphatase and phosphonate monoesterase still bound to the column. In control experiments none of these solvents caused irreversible loss of catalytic activity of either enzyme. In other experiments these enzymes were not eluted from phenoxyacetyl cellulose in high concentrations of salts (1.2 M ammonium sulfate) or 30% ethylene glycol. Other enzymes have been shown to be similarly strongly bound.

Alkaline phosphatase and phosphonate monoesterase can be completely eluted, with full activity, from phenoxyacetyl cellulose by buffer solutions containing 0.1% Triton X-100. These are examples of enzymes which are stable in the presence of this detergent; other similarly stable enzymes may also be eluted in this way.

EXAMPLE III

BATCHWISE TESTING OF PHENOXYACETYL CELLULOSE AS IMMOBILIZING AGENT FOR ALKALINE PHOSPHATASE

Phenoxyacetyl cellulose, prepared as previously described, was tested by a batchwise procedure rather than in a column as previously described. Dry phenoxyacetyl cellulose, sufficient to make a volume of 0.3 ml when wet, was suspended in a total of 5 ml of 0.1 M Tris, pH 9.0, and stirred vigorously. The phenoxyacetyl cellulose was sedimented in a desk-top centrifuge and the supernatant buffer removed by decantation. The phenoxyacetyl cellulose was washed twice more with 5 ml of the same buffer. Partially purified intestinal alkaline phosphatase, 10 $\mu$l of enzyme diluted in the same buffer, was added, mixed and warmed to 30° C. The enzyme was assayed in the presence of the phenoxyacetyl cellulose by addition of 1.0 ml of substrate mix previously warmed to 30° C. The suspended phenoxyacetyl cellulose was vigorously mixed once every minute. After 10 minutes incubation at 30° C the reaction was stopped by addition of 2.5 ml of 1 M bicarbonate containing 0.01 M $Na_3PO_4$; this effectively stops the enzyme reaction but does not denature the enzyme. After centrifugation of the suspended phenoxyacetyl cellulose the color generated in the aqueous supernatant was measured to obtain the amount of activity. Such measurements were always compared to an equivalent amount of enzyme assayed in the absence of any carrier. The suspended phenoxyacetyl cellulose was washed twice more with 5 ml of buffer and reassayed as previously described; then washed twice more with 5 ml of buffer and assayed a third time. After the third assays the phenoxyacetyl cellulose was washed with 5 ml of buffer containing 0.1% Triton X-100, then with 5 ml of buffer without Triton and reassayed. The results indicated that the enzymatic activity observed in the presence of phenoxyacetyl cellulose was, within experimental error, equivalent to that measured in the absence of carrier. At most, there was a difference of only 14% in the amounts of activity in the presence and absence of phenoxyacetyl cellulose. Therefore, the enzyme is fully active in the presence of phenoxyacetyl cellulose. The washing procedure after the first assay should have removed all but 0.1% of the enzyme if it were not bound to the carrier. The results of the second assays indicated that, instead of 99.9%, only approximately 5% of the enzymatic activity was lost. This is probably due to handling of the material rather than washing off of the activity from the carrier.

The third set of assays, after a further cycle of washes which again should have removed 99.9% of the activity unless it were firmly bound, in actuality removed only 8%, again indicating quite strong binding. In many experiments extensive washing has led to a loss of a very small amount of activity between assays; this seems to be aproximately the same regardless of what the carrier is or how many times the washes are carried out. It is probably due to an effect of the stop mix on the enzyme activity or due to mechanical loss of carrier during the handling procedures, rather than to elution of the enzyme off the carrier.

After washing with detergent, only a maximum of 4% of the activity was recovered. Thus, the dilute detergent solution essentially completely removed the enzyme from the carrier. In controlled experiments it has been shown repeatedly that the enzyme is completely stable in the presence of the detergent. This ability of Triton X-100 to elute the enzyme from the carrier has been utilized as a purification means; intestinal alkaline phosphatase and phosphonate monoesterase elute together from ion exchange columns such as DEAE cellulose, but have been separated quite nicely on columns of phenoxyacetyl cellulose by elution with a dilute solution of Triton X-100. Alkaline phosphatase elutes before phosphonate monoesterase under such conditions.

EXAMPLE IV

PREPARATION OF PHENOXYACETYL STRING (CELLULOSE) AND ITS UTILIZATION AS AN IMMOBILIZING AGENT FOR INTESTINAL ALKALINE PHOSPHATASE

The string utilized was soft cotton material, four threads twisted together; an effort was made to untwist the threads and loosen the string so that solvents might penetrate better. Eighteen inches of the loose untwisted string was suspended in a total of 100 ml of 1:1 pyridine:dimethylformamide and slowly, with vigorous stirring, 7 ml of phenoxyacetyl chloride (Aldrich) was added. After standing at room temperature overnight the string was recovered and extensively washed with water and stored in water in the refrigerator. A control string was similarly suspended in the solvents without addition of phenoxyacetyl chloride, and was tested in a parallel manner to the phenoxyacetylated string. For testing of the capacity of the modified and unmodified strings to adsorb proteins, four inches of each of the strings was suspended in 1 ml of a partially purified preparation of alkaline phosphatase from bovine intestine. After 20 minutes on ice the strings were removed and washed vigorously in a stream of deionized water. They were then cut into 1 inch sections and assayed by suspension in a conventional assay medium; at the same time small aliquots of the original enzyme solution were assayed for purposes of comparison. The data were calculated on the basis of the amount of alkaline phosphatase activity on 1 inch of string compared to the amount of alkaline phosphatase activity in 1 $\mu$l of the original enzyme solution. The phenoxyacetylated string was found to contain the equivalent of 4.8 $\mu$l of enzyme per inch of string; the control string which had been exposed to the same solvents but without phenoxyacetyl chloride contained the equivalent of only 0.6 $\mu$l of enzyme per inch of string. Therefore, phenoxyacetylation greatly enhances binding of the enzyme to the string. The phenoxyacetylated string was stored for eight days, half in a buffer solution and half in a moist condition in a test tube without buffer; although considerable loss of activity occurred, both still contained active enzyme. The sample stored in the absence of buffer retained the most activity. In other experiments similar phenoxyacetylated string with bound enzyme has been stored dry at room temperature for several weeks with retention of at least a sizable portion of its original activity.

EXAMPLE V

PREPARATION OF PHENOXYACETYL DERIVATIVES OF GLASS AND THEIR TESTING AS SUPPORTS FOR ADSORBING PROTEIN

Three different derivatives of glass were utilized. The chemical structure of these derivatives are shown below:

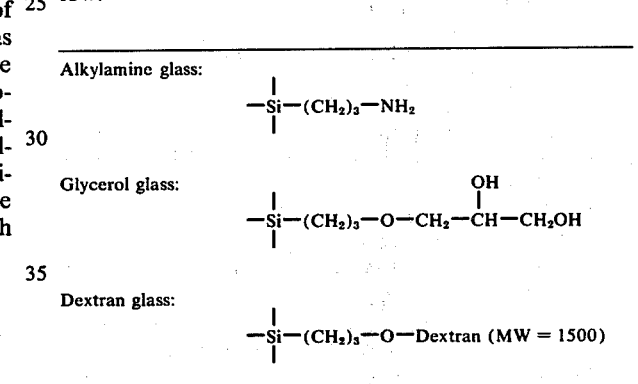

Two 3.0 gram samples of each glass derivative were placed in a small plastic bottle and 15 ml of pyridine were added to each. One sample of each type of glass was set aside as a control. To the remaining sample of each type of glass 1.0 ml of phenoxyacetyl chloride was added slowly with stirring. Heat was generated from all three samples; the alkylamine glass derivative turned yellow and the others turned dark reddish-orange. All samples were left overnight at room temperature and the next day were washed five times with approximately 25 ml each of 95% ethanol, along with the controls. After washing all samples twice with water they were stored in the cold room. For testing as immobilizing agents for intestinal alkaline phosphatase, a 0.3 ml (wet volume) sample of each of the glass derivatives, including controls and a sample of underivatized glass beads, was washed two times with 5 ml of buffer (0.1 M Tris, pH 9.0). Washing was done by allowing the glass beads to settle and then removing the supernatant fluid by suction aspiration through a Pasteur pipette. Diluted enzyme, 10 $\mu$l, was added to each sample and gently mixed. After warming to 30° C, the enzyme was assayed in the presence of the beads by addition of 1 ml substrate mix at 30° C, with stirring every minute. Incubations were stopped and read as previously described in Example III. The first set of assays, in which all of the enzyme was present and no washing had occurred, determined the effect of the glass derivatives on the activity of the added enzyme. The results indicated that in all samples the enzyme was essentially fully active; the measured activities ranged from 81–102% of those of the controls in which contained no glass derivatives. The glass derivatives were then washed two times with 5 ml portions of buffer and reassayed. If the enzyme had not been adsorbed, 99.9% of the activity should have been removed by the washings. The results of the second assays indicated that at least 98% of the enzyme was removed from all control samples, from the phenoxyacetylated alkylamine glass and from the control sample in which unmodified glass was utilized. In contrast, phenoxyacetylated dextran glass and phenoxyacetylated glycerol glass retained approximately 75% of the original activity through the washing procedure; therefore, the enzyme must have been strongly bound to these derivatives. After a further washing cycle identical to the first, these derivatives were assayed again with the finding that only approximately 6% of the activity was lost; at least 90% of the activity was retained throughout the wash. Again, the enzymes appear to be very strongly bound to these derivatives. The next wash cycle which was utilized included a wash with 5 ml of 0.1% Triton X-100 which effectively removes the enyzme from phenoxyacetyl cellulose (see Example III). Control experiments with phenoxyacetyl cellulose carried out at the same time as with these glass derivatives indicated that essentially all activity was released from phenoxyacetyl cellulose by this detergent. In contrast, the phenoxyacetylated glass derivatives retained almost 60% of their activity through the Triton X-100 wash. Thus, the enzyme appears to be even more strongly bound to the phenoxyacetylated cellulose. Another enzyme, subtilision (Carlsberg) has been shown to remain bound to phenoxyacetylated glycerol glass and phenoxyacetylated dextran glass when washed with 99% ethanol; after subsequent washing with aqueous buffer the enzyme was catalytically active.

These phenoxyacetyl glass derivatives were also tested with another enzyme, crystalline yeast inorganic pyrophosphatase. The assays for this enzyme are considerably different, but the wash procedures used were similar to those described above. Again, the first set of assays were done without washing to determine the effect of the glass derivatives on the activity of the added enzyme. The results obtained were quite different from those obtained with the alkaline phosphatase enzyme. Inorganic pyrophosphatase had previously been shown to bind strongly to phenoxyacetyl cellulose with consequent loss of essentially all of its activity. In contrast, the alkylamine glass appeared to be relatively innocuous to this enzyme; approximately 75% of the activity was expressed in the presence of phenoxyacetylated alkylamine glass as well as the control alkylamine glass. With the dextran glass about 50% of the total amount of activity was expressed in both the control and phenoxyacetylated derivative. With the glycerol glass derivative a large difference was observed between the control and the phenoxyacetylated forms; the control sample showed 100% of the activity; there is no effect of this glass derivative on the activity of the enzyme. In contrast, the phenoxyacetylated glycerol glass derivative essentially inactivated the enzyme. A maximum of 7% of the original activity was observed. Thus, the enzyme behaves in essentially the same manner toward phenoxyacetylated cellulose and phenoxyacetylated glycerol glass. That is, it is inactivated. After washing these glass derivatives to the extent that unless the enzyme were bound only 0.1% of the activity would remain, they were assayed again. No activity was observed in the glycerol glass derivatives even in the control in which 100% was observed without a wash. This means that the wash procedure is adequate to completely remove the activity unless it is bound; the enzyme is simply not bound at all to the control glycerol glass and it is inactivated by the phenoxyacetylated glycerol glass. The other two glass derivatives were somewhat anomalous. In both cases considerable activity, as much as 43% of the original, was retained by the control glass, so that there is weak binding of the enzyme to glass which has not been modified to make it especially hydrophobic. The phenoxyacetylated derivatives of both the dextran and alkylamine glass, however, retained more activity than did the controls so that, as previously observed, phenoxyacetylation does enhance the binding. These observations were repeated after a further washing cycle; the results were again similar. The interpretation of the results of the testing of inorganic pyrophosphatase on these glass derivatives is that phenoxyacetylation does enhance binding and certain derivatives can retain considerable activity in conditions where the enzyme is completely inactivated by phenoxyacetyl cellulose. However, the phenoxyacetylation is not completely specific; there is some binding, though weaker, to the derivatives before they are phenoxyacetylated. It should be noted that this enzyme, yeast inorganic pyrophosphatase, is somewhat anomalous. Of all of the enzymes which have been tested on phenoxyacetyl cellulose, it is the only one which is inactivated by exposure to this material. It is similarly inactivated by exposure to phenoxyacetyl glycerol glass. It is partially inactivated by exposure to all 3 of the glass derivatives; however, some of these show promise as binding agents for even very sensitive enzyme. All of the other enzymes including maize and spinach leaf inorganic pyrophosphatase, E. coli alkaline phosphatase, pancreatic chymotrypsin, and bovine intestinal phosphonate monoesterase, when tested against phenoxyacetyl cellulose behave similarly to the intestinal alkaline phosphatase which has been described in Examples II–IV above. Presumably these enzymes will also behave similarly to intestinal alkaline phosphatase on the phenoxyacetylated glass derivatives described in Example IV.

The chemical structure of phenoxyacetyl cellulose is as follows:

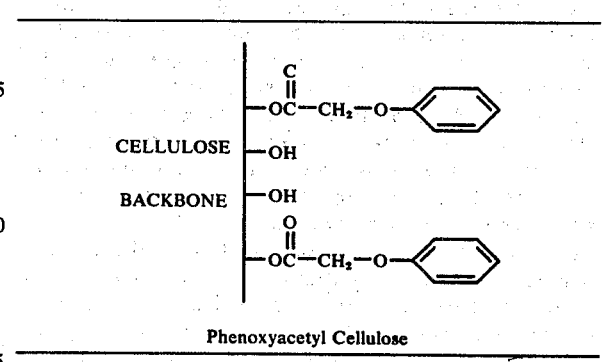

Phenoxyacetyl Cellulose

As noted above, various proteins behave somewhat differently with respect to a particular hydrophobic derivative. Indeed, this selectivity is useful when such derivatives are used for purification purposes. Moreover, a particular enzyme behaves somewhat differently with respect to the material which supports the hydrophobic derivative, as noted above. Obviously, many other materials could be modified with hydrophobic derivatives for this purpose. The obvious candidates include agarose gel and polyacrylamide gel, both of which have been used as supports for affinity chromatography and enzyme immobilization. It is to be realized of course that conditions appropriate for preparing hydrophobic derivatives of these materials might differ from the conditions described hereinabove with respect to the materials specified herein.

All the derivatives described hereinabove have been derivatives obtained by using phenoxyacetyl chloride. Many other hydrophobic materials might also be suitable. Experiments to this effect have been carried out with lauryl chloride, benzoyl chloride, acetyl chloride and phenylbutryl chloride. With present data, it would appear that the aromatic derivatives result in stronger binding than the aliphatic derivatives. In the aromatic series, phenoxyacetyl derivatives clearly bind proteins more strongly than do benzoyl derivatives and it seems likely that a certain distance of the aromatic group from the support is necessary for optimum binding. In addition, by ending in an inert hydrocarbon, as does phenoxyacetyl cellulose as shown hereinabove, this makes removal substantially impossible in a solution of salt (unlike an ionic type of binding).

The chemical structure for lauryl cellulose, benzoyl cellulose, acetyl cellulose and phenylbutryl cellulose are as follows:

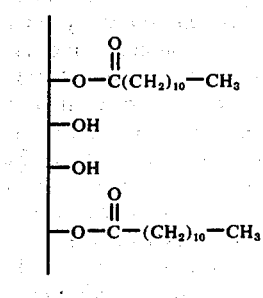

Lauryl Cellulose

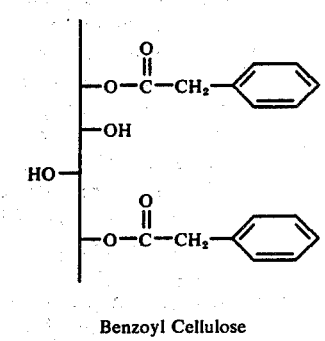

Benzoyl Cellulose

-continued

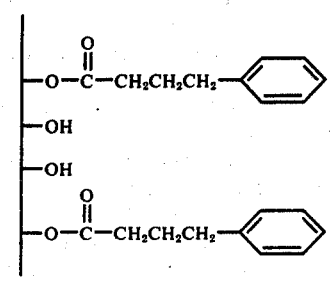

Phenylbutryl Cellulose

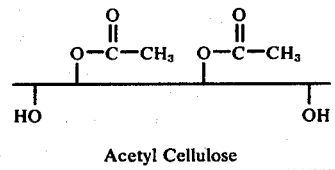

Acetyl Cellulose

Another type of alternative is available with cellulose as the support material which is not available with other types of supports. Cellulose is available in many different forms: microcrystalline fibers, power, thread, string, gauze, cloth, paper, and cotton balls. This versatility makes available many new applications of cellulose as a support. No other material is available in such a variety of forms; however, this invention is not meant to be limited to any one particular form of the support material.

The support materials of this invention can be prepared more readily and more cheaply than conventional ionic derivatives of cellulose or other supports and more readily and cheaply than other hydrophobic derivatives that have been described. The adsorption process is relatively simple compared to the necessity for covalent attachment of enzymes; moreover, essentially full activity is expressed by the bound enzyme when adsorbed. This is usually not the case with covalently attached enzymes. These hydrophobically-modified materials also appear to have relatively high capacity for binding proteins. Cellulose as a support has the advantages of chemical inertness and stability as well as availability in a large number of different physical forms as described above. Glass has the advantage of stability and the lack of conformability of the bed, leading to good flow rates when packed into columns.

The following are applications of this invention of which at least some have been reduced to practice:

a. Chromatographic purification of proteins: As mentioned previously, intestinal alkaline phosphatase and phosphatase monoesterase are being routinely separated chromatographically by adsorption on a column of phenoxyacetyl cellulose and elution with a dilute solution of Triton X-100. This technique is used in the purification of maize leaf inorganic pyrophosphatase. This technique should be applicable to many other systems.

b. Removal of amphipathic materials from protein solutions: In the presence of amphipathic materials such as detergents, many proteins are not adsorbed to derivatives such as phenoxyacetyl cellulose. The amphipathic materials such as detergents and/or phenolic compounds in plant leaf extracts are readily removed from solutions by passage over a column of phenoxyacetyl cellulose. At least in some cases passages of the extract, after removal of the amphipathic materials, over a fresh column of phenoxyacetyl cellulose subsequently results in strong adsorption of the protein.

c. Adsorption of antibodies for use in radioimmune assays.

d. As immobilization support for enzymes: Subject to the condition that the enzyme behave in the manner of those mentioned in this application as being successfully tested, enzymes immobilized as herein described can be utilized in many of the applications suggested for conventionally immobilized enzymes. Since these have been well publicized, in the following discussion emphasis will be given to potential novel applications arising from the use of enzymes immobilized onto various physical forms of cellulose. It should be mentioned that some of the derivatives which have been found to bind enzymes only moderately strongly might be useful for applications in which a timed release of enzyme in the soluble form is desired.

e. Enzymes immobilized on derivatized filter paper or bulk paper products: Enzymes on filter paper provide a convenient and rapid way of carrying out enzyme treatments. The enzyme treatment and the filtration used in claryifying certain food products such as fruit juices and cider could thus be combined into a single step. This would be applicable to any process in which the filtered material could be solubilized by enzyme digestion. Digestion of the material which would otherwise build up and clog the filter would thus greatly increase the volume of material which could be filtered without stopping the process to replace the filter. Flow rates should also be correspondingly enhanced.

Enzymes could also be conveniently and economically bound to high-volume paper products such as cleansing tissue, paper towels, or toilet paper, if desirable.

f. Enzymes immobilized on derivatized thread or string: Enzymes immobilized in these forms could provide a significant advantage over currently-employed soluble enzymes in analytical procedures in clinical and research laboratories. Such procedures in clinical laboratories include measurements of alcohol, glucose, lactic acid, pyruvate, urea nitrogen, transaminase and others; in biomedical and biomedical research the appropriate enzymes used as accessories include alkaline phosphatase, nucleases, various proteases, lipases and catalyse as well as others. Enzyme immobilized on derivatized string could be added to and removed from assays without otherwise affecting the composition of the mixture being analyzed. The enzyme activity would be standardized and sold in terms of units of activity per inch of string; this would permit unskilled workers to use standard amounts of enzyme without the necessity for making precise measurements of catalytic activity. The enzyme of course could be utilized over and over again. The string could be arranged in several different configurations: it could be simply submerged in the solution in which it is to be used; it could be attached to a stirring device; it could be fixed in a stream which is flowing past, or it could be arranged in the form of a wick attached to a small funnel, so that the solution assayed could percolate down the string and drip off into a vial. This configuration would seem to be especially useful for assays carried out in a clinical laboratory.

One very common utilization would be the enzyme alkaline phosphatase, which is routinely employed in sequencing studies of polynucleotides. Once this enzyme is added in a soluble form, subsequent operations are severely limited because it obscures results at other stages in the analysis. There are no known effective means of selectively inactivating this enzyme. Utilization of this enzyme in a bound form on string or a cotton ball would allow it to be completely removed when desired, without otherwise affecting the solution. This would be of considerable aid to nucleotide chemists, and would seem to be an application which could be immediately exploited since we have considerable experience with this enzyme bound to these derivatives. This could also readily be done with other enzymes routinely used as accessories in biochemical research.

A potentially very important application of enzymes immobilized on string would be in teaching the rudiments of chemical catalysis and enzyme chemistry to high school, junior high, and even grade school students. Soluble enzymes used to demonstrate the desired concepts require somewhat complex laboratory equipment (pipettes, etc.) and experience in using it. The same enzymes immobilized on string could be used to teach these concepts with only a ruler to measure out an amount of enzyme. Thus, instead of a demonstration of the concept by the teacher, the student himself could do the experiment, with increased educational benefit.

g. Enzymes immobilized on derivatized cloth or gauze: "Self-cleaning" cloth could result from immobilization of a mixture of hydrolytic enzymes on the material; for example, a soiled butcher's apron prepared from this material could be cleaned merely by soaking overnight in room temperature water, followed by rinsing. The absorbent capacity of sanitary napkins could be much more completely utilized by incorporating on the surface a layer of gauze containing immobilized enzymes capable of digesting and solubilizing the mucous secretions which otherwise accumulate on the surface and prevent complete adsorption of the liquid. Since proteolytic enzyme treatment has been helpful in wound debridement to remove scar tissue and promote healing, this application seems ideal for enzyme immobilized on bandages. Diagnostic tests might be simplified by immobilization of appropriate enzymes directly on bandages or diapers. Cellulase immobilized on a cellulose thread might be utilized as a self-dissolving surgical thread.

h. Enzymes immobilized on derivatized membranes: A cellulase enzyme immobilized on a cellulose-based membrane might result in a self-dissolving packaging material. Certainly, enzymes immobilized on one side of a semi-permeable membrane would be of great interest in studies of cellular active transport, and would have medical applications such as in dialysis units. Enzymes immobilized inside capillary tubes would provide a rapid and convenient method of treatment.

i. Enzymes immobilized on derivatized cotton balls: Degradative enzymes on such supports might be used as filters for sterilization of air (in masks, etc.)

water streams (for example, in aquaria). In addition, see above applications.

j. Enzymes immobilized on derivatized powder, small beads, or small fibers (as in cellulose derivatives presently used for chromatography): The above suggestions do not preclude the utilization of these conventional forms of cellulose and other materials for protein and/or enzyme immobilization.

k. For removing proteins from reaction mixtures or extracts of biological materials by adsorption on hydrophobically-modified insoluble supports. Such removal would not dilute or otherwise change the composition of the liquid. Proteins in very dilute solutions might be concentrated in this way. For example, passage of a large volume of urine through a column of hydrophobically-derivatized support such as phenoxyacetyl cellulose should remove and bind all the trace enzyme and protein components. Elution with a mild detergent would then release these in a concentrated form which would be much more readily assayed (as in clinical tests) or utilized as a source of desired hormone or other factors.

l. For modifying small water-soluble materials hydrophobically so that they will bind proteins. Water-soluble dextrans could be modified with these hydrophobic materials and used to bind such things as hormones, like insulin, to increase their stability, lifetime in the body, and/or biological potency. Enzymes adsorbed on hydrophobic derivatives of water-soluble dextrans might be advantageous for therapy, or for modification of immunological properties. Hydrophobic derivatives of small hydrophilic sugars such as sucrose could be used as protein eluants from chromatographic columns of hydrophobic cellulose derivatives. Non-physiological materials which would otherwise cause an immune reaction on exposure to body fluids might be protected by hydrophobic modification and subsequent adsorption of human serum albumin.

m. The technique for hydrophobic derivatization is sufficiently simple and mild that with modification, it should be possible to hydrophobically derivatize the surface of bacteria, erythrocytes, viruses or other biological materials, so that they would strongly bind proteins and/or enzymes. This technique has important potential applications. For example, it may be possible to prevent foreign materials such as erthrocytes from some other organism from causing an immunological response in the human body, by immobilizing human serum albumin on their surface. Penetration of vial DNA into cultured cells may be aided by immobilizing appropriate digestive enzymes on the viral coat; this might lead to a breakthrough in transfer of genetic information into higher cells.

As can be seen from the foregoing, this invention provides a novel method and use for strong noncovalent binding of proteins to a hydrophobic support material.

What is claimed is:

1. A method of noncovalent binding of proteins to support materials, said method comprising:
    selecting a hydrophilic support material having hydroxyl or amino groups;
    treating said selected support material by chemically modifying said material by treatment with phenoxyacetyl chloride to make said support material hydrophobic in nature to thus form a hydrophobic derivative of said support material suitable for immobilizing proteins when exposed to said treated hydrophobic material;
    selecting a protein that is capable of being immobilized on said treated hydrophobic material with said protein having a capacity for subsequent biological activity; and
    exposing said selected protein to said treated hydrophobic material to cause said protein to be effectively immobilized on said treated hydrophobic material by adsorption and substantially without impairing said subsequent biological activity of the protein.

2. The method of claim 1 wherein said method includes the step of selecting said hydrophilic support material from carbohydrate polymers and inorganic materials.

3. The method of claim 2 wherein said carbohydrate polymer is cellulose.

4. The method of claim 2 wherein said inorganic material is glass.

5. The method of claim 1 wherein said method includes exposing said protein to said support material in an aqueous environment.

* * * * *